(12) United States Patent
Pinkos et al.

(10) Patent No.: US 8,247,580 B2
(45) Date of Patent: Aug. 21, 2012

(54) PROCESS FOR PREPARING ε-CAPROLACTONE

(75) Inventors: Rolf Pinkos, Bad Duerkheim (DE); Gerd-Dieter Tebben, Mannheim (DE); Thomas Krug, Worms (DE); Tilman Sirch, Schifferstadt (DE); Todd C Spengeman, Sugar Land, TX (US); Stephanie A. Bejune, Angleton, TX (US); Jeffrey T. Andress, Lake Jackson, TX (US); Todd Gasiorowski, Lake Jackson, TX (US)

(73) Assignee: BASF SE, Ludwigshafen (DE)

( * ) Notice: Subject to any disclaimer, the term of this patent is extended or adjusted under 35 U.S.C. 154(b) by 138 days.

(21) Appl. No.: 12/741,383

(22) PCT Filed: Oct. 28, 2008

(86) PCT No.: PCT/EP2008/064608
§ 371 (c)(1),
(2), (4) Date: May 5, 2010

(87) PCT Pub. No.: WO2009/059913
PCT Pub. Date: May 14, 2009

(65) Prior Publication Data
US 2010/0240913 A1    Sep. 23, 2010

Related U.S. Application Data

(60) Provisional application No. 60/985,424, filed on Nov. 5, 2007.

(51) Int. Cl.
*C07D 313/00* (2006.01)
(52) U.S. Cl. ...................................................... 549/266
(58) Field of Classification Search .................... 549/266
See application file for complete search history.

(56) References Cited

U.S. PATENT DOCUMENTS

| | | | |
|---|---|---|---|
| 5,068,361 A | | 11/1991 | Richter et al. |
| 5,981,769 A | * | 11/1999 | Baur et al. ............... 549/266 |
| 6,426,438 B1 | | 7/2002 | Fischer et al. |
| 2004/0040829 A1 | | 3/2004 | Gall et al. |

FOREIGN PATENT DOCUMENTS

| | | |
|---|---|---|
| DE | 38 23 213 | 1/1990 |
| DE | 197 50 532 | 5/1999 |
| DE | 101 00 552 | 7/2002 |
| DE | 103 08 489 | 9/2004 |
| DE | 10308489 A1 * | 9/2004 |
| GB | 1 140 184 | 1/1969 |
| GB | L140184 * | 1/1969 |
| WO | 97 31883 | 9/1997 |

OTHER PUBLICATIONS

U.S. Appl. No. 13/131,310, filed May 26, 2011, Pinkos, et al.
U.S. Appl. No. 13/133,006, filed Jun. 6, 2011, Abillard, et al.
U.S. Appl. No. 13/257,496, filed Sep. 19, 2011, Pinkos, et al.
U.S. Appl. No. 13/258,166, filed Sep. 21, 2011, Pinkos, et al.
U.S. Appl. No. 13/381,116, filed Dec. 28, 2011, Kunst, et al.
"Ullmann's Encyclopedia of Industrial Chemistry", Coronary Therapeutics to Display Technology, vol. A 8, Fifth, Completely Revised Edition, pp. 25-59, (1987).
Hauben-Weyl, Methoden der Organischen Chemie [Methods of Organic Chemistry] vol. IV/1C, pp. 16-26 (1980).

* cited by examiner

*Primary Examiner* — Nizal Chandrakumar
(74) *Attorney, Agent, or Firm* — Oblon, Spivak, McClelland, Maier & Neustadt, L.L.P.

(57) ABSTRACT

The present invention provides a process for preparing ε-caprolactone in a purity of more than 99% by cyclizing 6-hydroxycaproic esters in the liquid phase at from 150 to 400° C. and from 1 to 1020 hPa abs., and removing and condensing the compounds which are volatile under cyclization conditions, which comprises thermally treating the remaining bottom product of the cyclization in at least one further reactor, removing and condensing volatile compounds and obtaining ε-caprolactone by distillation from the condensates.

20 Claims, 1 Drawing Sheet

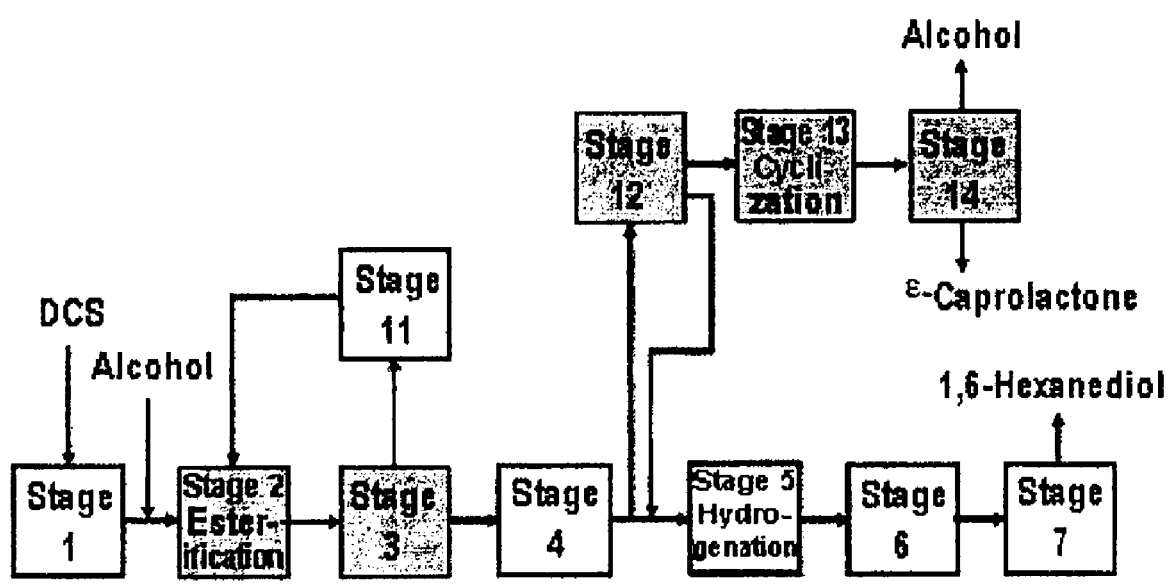

PROCESS FOR PREPARING ε-CAPROLACTONE

The invention relates to an improved process for preparing ε-caprolactone in a purity of more than 99% by cyclizing 6-hydroxycaproic esters in the liquid phase at from 150 to 400° C. and from 1 to 1020 hPa abs., and removing and condensing the compounds which are volatile under cyclization conditions, in which the remaining bottom product of the cyclization is thermally treated in at least one further reactor, volatile compounds are removed and condensed and ε-caprolactone is obtained by distillation from the condensates.

ε-Caprolactone or the polycaprolactones prepared therefrom by polyaddition serve to prepare polyurethanes.

It is known that 6-hydroxycaproic esters can be cyclized to caprolactone in the gas or liquid phase. For instance, DE 38 23 213 describes the cyclization of 6-hydroxycaproic esters to give caprolactone in the gas phase in the presence of oxidic catalysts and inert carrier gases.

Additionally known from WO 97/31883 is a process for preparing 1,6-hexanediol and ε-caprolactone from a carboxylic acid mixture which comprises adipic acid, 6-hydroxycaproic acid and small amounts of 1,4-cyclohexanediols and is obtained as a by-product of the oxidation of the cyclohexane to cyclohexanone/cyclohexanol with oxygen or oxygen-comprising gases and is obtained by water extraction of the reaction mixture.

The aqueous solutions of carboxylic acids which are formed as by-products in the oxidation of cyclohexane to cyclohexanol and cyclohexanone (cf. Ullmann's Encyclopedia of Industrial Chemistry, 5th Ed., 1987, Vol. A8, p. 49) are referred to hereinafter as dicarboxylic acid solution (DCS), comprise (calculated without water in % by weight) generally between 10 and 40% adipic acid, between 10 and 40% 6-hydroxycaproic acid, between 1 and 10% glutaric acid, between 1 and 10% 5-hydroxyvaleric acid, between 1 and 5% 1,2-cyclohexanediols, between 1 and 5% 1,4-cyclohexanediols, between 2 and 10% formic acid, and a multitude of further mono- and dicarboxylic acids, esters, oxo and oxa compounds whose individual contents generally do not exceed 5%. Examples include acetic acid, propionic acid, butyric acid, valeric acid, caproic acid, oxalic acid, malonic acid, succinic acid, 4-hydroxybutyric acid and gamma-butyrolactone.

After dewatering, the aqueous solutions are esterified with a low molecular weight alcohol to the corresponding carboxylic esters, the resulting esterification mixture is freed of excess alcohol and low boilers in a first distillation stage. From the bottom product, in a second distillation stage, a separation into an ester fraction essentially free of 1,4-cyclohexanediols and a fraction comprising at least the majority of the cyclohexanediols is obtained. A third distillation stage affords a fraction comprising essentially 6-hydroxycaproic esters (stage 2), which is cyclized to ε-caprolactone in the gas phase, preferably in the liquid phase.

The stream comprising essentially 6-hydroxycaproic esters is heated under reduced pressure to temperatures of more than 200° C., which cyclizes 6-hydroxycaproic esters to caprolactone, and pure caprolactone can be obtained by distillation from the cyclization product. The liquid phase cyclization can be effected without catalyst, but is preferably performed in the presence of a catalyst. In some cases, it is advantageous to perform the cyclization reaction in the presence of high-boiling mono-, di- or polyols.

The reaction products, predominantly caprolactone and esterification alcohol, are removed from the reaction mixture in gaseous form and condensed. Fractional distillation provides caprolactone from the condensate.

A disadvantage is that, especially when the process is performed on the industrial scale, to avoid very long residence times and resulting expensive reaction space, only caprolactone yields of up to 90%, generally only up to 80%, are achieved. This is attributable, among other factors, to oligomerization and polymerization side reactions in which 6-hydroxycaproic esters of the formula HO—$(CH_2)_5$—COOR (R is, for example, a $C_1$- to $C_4$-alkyl radical) form dimers of the formula $HOCH_2$—$(CH_2)_4$—COO—$(CH_2)_5$—COOR, from which oligomers and polymers can form by reaction with further hydroxy esters.

When the 6-hydroxycaproic esters still comprise diesters, especially adipic diesters, which may also be unsaturated, it is possible, for example, in the case of the dimethyl ester for the dimeric ester $CH_3OOC$—$(CH_2)_4$—$COO(CH_2)_5$—$COOCH_3$ to form, from which oligomers and polymers may likewise form with incorporation of further 6-hydroxy ester molecules. In the presence of these diesters, especially when they exceed contents of 1%, the yield of caprolactone is reduced considerably, in some cases below 70%, especially in the case of short residence times.

It was therefore an object of the invention to provide a process for liquid phase preparation of ε-caprolactone in a purity of more than 99% proceeding from 6-hydroxycaproic esters or mixtures comprising them, in which, especially in industrial performance, higher caprolactone yields (based on the 6-hydroxycaproic esters used in the cyclization) are achieved.

This object is achieved by a process for preparing ε-caprolactone in a purity of more than 99% by cyclizing 6-hydroxycaproic esters in the liquid phase at from 150 to 400° C. and from 1 to 1020 hPa abs., and removing and condensing the compounds which are volatile under cyclization conditions, which comprises thermally treating the remaining bottom product of the cyclization in at least one further reactor, removing and condensing volatile compounds and obtaining ε-caprolactone by distillation from the condensates.

In the further reactor or reactors, the thermal treatment can be effected under the pressure and temperature conditions of the cyclization, but is preferably thermally treated at a higher temperature, for example at a temperature of 50° C. higher. It is also additionally possible to vary the pressure; preference is given to establishing a lower pressure than in the cyclization.

The bottom products of the caprolactone preparation are complex mixtures of oligomeric and polymeric esters, which generally comprise 6-hydroxycaproic acid, adipic acid, unsaturated adipic acid and diol units such as 1,4-cyclohexanediols. However, it is also possible for other alcohol components, for example 1,5-pentanediol, 1,6-hexanediol, 1,4-cyclohexanedimethanol, nonanol, tridecanol or pentadecanol to be present, which have either been added beforehand and/or may be intrinsic to the system, for example 1,5-pentanediol.

It was therefore surprising that additional, remarkably large amounts of ε-caprolactone can still be obtained from the bottom products of the cyclization to ε-caprolactone by heating, and that the high purity requirements on the product of purities>99% can additionally be achieved.

BRIEF DESCRIPTION OF THE DRAWINGS

FIG. 1 schematically represents a preparation of 6-hydroxycaproic esters, broken down into stages, by esterifying a carboxylic acid mixture which comprises adipic acid, 6-hydroxycaproic acid, and small amounts of 1,4-cyclohexanediols.

According to the invention, the bottom product of the 6-hydroxycaproic ester cyclization which is nonvolatile under the conditions of the cyclization can be subjected to a thermal treatment batchwise or continuously in at least one further reactor, i.e. a reactor other than the cyclization reactor. The compounds which are now volatile and distill off are condensed. Additional caprolactone is obtained from the condensate by distillation and increases the overall caprolactone yield.

The thermal treatment is effected at temperatures of from 150 to 400° C., preferably from 180 to 350° C., more preferably from 190 to 330° C., and pressures of from 1 to 1020 hPa abs., preferably from 2 to 500 hPa, more preferably from 5 to 200 hPa. The thermal treatment of the bottom product of the cyclization is effected generally at the same temperature or preferably at a temperature up to 100° C. higher than the cyclization of the 6-hydroxycaproic esters. It is particularly preferred to perform the thermal treatment of the bottom product from the cyclization at temperatures up to 50° C. higher and especially preferably up to 30° C. higher than in the 6-hydroxycaproic ester cyclization. The thermal treatment can be effected continuously or batchwise. The residence time is generally from 0.1 to up to 24 hours, preferably up to 15 hours, more preferably up to 10 hours. The reaction pressure may correspond to the pressure of the cyclization, but a lower pressure is preferred. In absolute terms, it is preferably below 50 hPa, more preferably between 1 and 30 hPa.

The reactors used for the thermal treatment may, for example, be mixed vessels with an attached distillation column, wiped-blade evaporators (Sambay evaporators) or falling-film evaporators. It is also preferred not to drive out the gaseous reaction products of the thermal treatment in one stage, but rather to use a separating apparatus having at least one theoretical plate and partial liquid product reflux. This surprisingly increases the yield of caprolactone. It is also possible to perform the thermal treatment in a reaction column.

A solvent can be added to the bottom product of the cyclization.

In a preferred embodiment, high-boiling mono-, di- or polyol is added to the bottom product of the cyclization before or during the thermal treatment. "High-boiling" is understood to mean mono-, di- or polyols having boiling points preferably above the boiling point of caprolactone under the given reaction pressures. The mono-, di- or polyol used may be decanol, undecanol, tridecanol, pentadecanol, octadecanol, 1,4-butanediol, 1,5-pentanediol, 1,6-hexanediol, 1,4-cyclohexanediols, butylethylpropane-diol, neopentyl glycol, triethylene glycol, tetraethylene glycol, trimethylolpropane and glycerol. Likewise suitable are high-boiling mono-, di- or polyol-comprising mixtures which are obtained as distillation residues in the synthesis of mono-, di- or polyol, for example distillation residues which are obtained in the synthesis of nonanol or tridecanol/pentadecanol. These high-boiling mono-, di- or polyols are initially charged and/or added or metered separately to the reaction mixture, for example in each case in concentrations of from 0.1 to 90% by weight, preferably from 1 to 60% by weight, more preferably from 5 to 30% by weight.

In a further preferred embodiment, the thermal treatment of the bottom product of the cyclization is performed in the presence of a catalyst. In particular when a homogeneously dissolved catalyst is used in the cyclization, it is possible for this catalyst still to be present in the thermal treatment, but a further catalyst may also be added.

Suitable catalysts for the thermal treatment are the catalysts which are also known per se for the cyclization of the 6-hydroxycaproic esters. Suitable catalysts are catalysts which may be present in homogeneously dissolved or heterogeneous form. Examples are alkali metal and alkaline earth metal hydroxides, oxides, carbonates, alkoxides or carboxylates, Lewis acids or Lewis bases, preferably from main group III. and IV. or transition group I. to VIII. of the Periodic Table of the Elements, or oxides of rare earth metals or mixtures thereof. Examples include magnesium oxide, zinc oxide, boron trioxide, titanium dioxide, silicon dioxide, tin dioxide, bismuth oxide, copper oxide, lanthanum oxide, zirconium dioxide, vanadium oxides, chromium oxides, tungsten oxides, iron oxides, cerium oxide, aluminum oxide, hafnium oxide, lead oxide, antimony oxide, barium oxide, calcium oxide, sodium hydroxide, potassium hydroxide, neodymium oxide. It is also possible to use mixtures of oxides, which may be mixtures of the individual components or else mixed oxides, as occur, for example, in zeolites, aluminas or heteropolyacids. Preference is given to Lewis acids or bases based on aluminum, zirconium or titanium.

Advantageously, a catalyst hourly space velocity of from 0.01 to 40 g, preferably from 0.05 to 20 g, especially from 0.07 to 10 g of reactant (6-hydroxycaproic ester) per g of catalyst and hour is maintained. Homogeneous catalysts are used in a concentration of typically from 10 to 10 000 ppm, preferably from 5 to 5000 ppm, more preferably from 100 to 1000 ppm.

During the thermal treatment, volatile compounds are obtained as top products in the form of mixtures which comprise ε-caprolactone as the main product as well as low boilers, for example lower alcohols.

To further enhance the ε-caprolactone yield, it may be advisable to recycle the bottom product to the thermal treatment or to subject it to a further separate thermal treatment.

In the process according to the invention, the bottom product of the cyclization of the 6-hydroxycaproic esters to ε-caprolactone is used for the thermal treatment.

Useful 6-hydroxycaproic esters are generally esters of the alkanols having from 1 to 12 carbon atoms, cycloalkanols having from 5 to 7 carbon atoms, aralkanols having from 7 to 8 carbon atoms or phenols having from 6 to 8 carbon atoms. It is possible to use methanol, ethanol, propanol, isopropanol, n- or isobutanol or else n-pentanol or isopentanol or mixtures of the alcohols, but preferably alcohols having from 1 to 4 carbon atoms, more preferably methanol. Diols such as butanediol or pentanediol are also useful in principle. The ester groups in the 6-hydroxycaproic esters may be the same or different. The particularly preferred reactant is methyl 6-hydroxycaproate.

The 6-hydroxycaproic esters can be prepared, for example, according to DE-A 197 50 532, which is explicitly incorporated by reference here and is incorporated into the present application.

According to DE-A 197 50 532, 6-hydroxycaproic esters are obtained by catalytic hydrogenation of adipic diesters or reactant streams which comprise these esters as essential constituents, distilling the hydrogenation effluent and removing hexanediol and adipic diesters.

The hydrogenation is preferably performed in the liquid phase. The hydrogenation catalysts used in this process are generally heterogeneous, but also homogeneous catalysts suitable for hydrogenating carbonyl groups. They may be used either in fixed bed or mobile form, for example in a fluidized bed reactor. Examples thereof are described, for example, in Houben-Weyl, "Methoden der Organischen Chemie" [Methods of Organic Chemistry], Volume IV/1c, p. 16 to 26. Among the hydrogenation catalysts to be used, preference is given to those which comprise one or more elements of group I b, VI b, VII b and VIII b, and also III a, IV a and V a, of the Periodic Table of the Elements, especially copper, chromium, rhenium, cobalt, rhodium, nickel, palladium, iron, platinum, indium, tin and/or antimony. Particular preference is given to catalysts which comprise copper, cobalt and/or rhenium.

In addition, the preparation of the 6-hydroxycaproic esters can be effected according to WO 97/31883, which is referred to here explicitly and is incorporated here into the present application.

According to WO 97/31883, the 6-hydroxycaproic ester are prepared by esterifying a carboxylic acid mixture which comprises adipic acid, 6-hydroxycaproic acid and small amounts of 1,4-cyclohexanediols and is obtainable as a by-product of the oxidation of cyclohexane to cyclohexanone/cyclohexanol with oxygen or oxygen-comprising gases by water extraction of the reaction mixture with a low molecular weight alcohol to give the corresponding carboxylic esters, and separating the esterification mixture thus obtained in at least one distillation stage.

In a preferred embodiment, methyl 6-hydroxycaproate is obtained by
freeing the resulting esterification mixture of excess methanol and low boilers in a first distillation stage,
from the bottom product, in a second distillation stage, performing a separation into an ester fraction essentially free of 1,4-cyclohexanediols and a fraction comprising at least the majority of the 1,4-cyclohexanediols,
removing the methyl 6-hydroxycaproate stream from the ester fraction in a third distillation stage.

For better understanding, the process for preparing ε-caprolactone is explained according to WO 97/31 883 in FIG. 1, in which the individual process steps are broken down into further stages, of which stages 2, 3, 4 and 12, 13 and 14 are essential for the process for preparing ε-caprolactone, and stages 3 and 4 may also be combined.

The dicarboxylic acid solution (DCS) is generally an aqueous solution having a water content of from 20 to 80%. Since an esterification fraction is an equilibrium reaction in which water forms, it is advisable, especially in the case of esterification with methanol, for example, to remove water from the reaction, in particular when water cannot be removed during the esterification reaction, for example by azeotropic means. The dewatering in stage 1 can be effected, for example, with a membrane system, or preferably by means of a distillation apparatus in which water is removed via the top and higher monocarboxylic acids, dicarboxylic acids and 1,4-cyclohexanediols via the bottom at from 10 to 250° C., preferably from 20 to 200° C., more preferably from 30 to 200° C., and a pressure of from 1 to 1500 hPa, preferably from 5 to 1100 hPa, more preferably from 20 to 1000 hPa. The bottom temperature is preferably selected such that the bottom product can be drawn off in liquid form. The water content in the bottom of the column may be from 0.01 to 10% by weight, preferably from 0.01 to 5% by weight, more preferably from 0.01 to 1% by weight.

The water can be removed in such a way that the water is obtained in predominantly acid-free form, or the lower monocarboxylic acids present in the DCS—essentially formic acid—can be distilled off for the most part with the water in order that they do not bind any esterification alcohol in the esterification.

Alcohol ROH having from 1 to 10 carbon atoms can also be added to the carboxylic acid stream from stage 1. It is possible to use methanol, ethanol, propanol or isopropanol, or mixtures of the alcohols, but preferably methanol, on the one hand, or $C_4$ and higher alcohols, especially having from 4 to 8 carbon atoms and preferably n- or isobutanol or else n-pentanol or isopentanol on the other hand. The mixing ratio of alcohol to carboxylic acid stream (mass ratio) may be from 0.1 to 30, preferably from 0.2 to 20, more preferably from 0.5 to 10.

This mixture passes as a melt or solution into the reactor of stage 2, in which the carboxylic acids are esterified with the alcohol. The esterification reaction can be performed at from 50 to 400° C., preferably from 70 to 300° C., more preferably from 90 to 200° C. It is possible to apply an external pressure, but preference is given to performing the esterification reaction under the autogenous pressure of the reaction system. The esterification apparatus used may be one stirred tank or flow tube, or it is possible in each case to use a plurality. The residence time needed for the esterification is between 0.3 and 10 hours, preferably from 0.5 to 5 hours. The esterification reaction can proceed without addition of a catalyst, but preference is given to increasing the reaction rate by adding a catalyst. The catalyst may be a homogeneously dissolved catalyst or a solid catalyst. Examples of homogeneous catalysts include sulfuric acid, phosphoric acid, hydrochloric acid, sulfonic acids such as p-toluenesulfonic acid, heteropolyacids such as tungstophosphoric acid, or Lewis acids, for example aluminum, vanadium, titanium, boron compounds. Preference is given to mineral acids, especially sulfuric acid. The weight ratio of homogeneous catalyst to carboxylic acid melt is generally from 0.0001 to 0.5, preferably from 0.001 to 0.3.

Suitable solid catalysts are acidic or superacidic materials, for example acidic or superacidic metal oxides such as $SiO_2$, $Al_2O_3$, $SnO_2$, $ZrO_2$, sheet silicates or zeolites, all of which may be doped with mineral acid esters such as sulfate or phosphate for acid strengthening, or organic ion exchangers with sulfonic acid or carboxylic acid groups. The solid catalysts may be arranged as a fixed bed or be used as a suspension.

The water formed in the reaction is appropriately removed continuously, for example by means of a membrane or by distillation.

The completeness of the conversion of the free carboxyl groups present in the carboxylic acid melt is determined with the acid number measured after the reaction (mg KOH/g). Minus any acid added as a catalyst, it is from 0.01 to 50, preferably from 0.1 to 10. Not all carboxyl groups present in the system need be present as esters of the alcohol used, but rather a portion may be present in the form of dimeric or oligomeric esters with the OH end of the hydroxycaproic acid.

The esterification mixture is fed into stage 3, a membrane system or preferably a distillation column. When a dissolved acid has been used as a catalyst for the esterification reaction, the esterification mixture is appropriately neutralized with a base, in which case from 1 to 1.5 base equivalents are added per acid equivalent of the catalyst. The bases used are generally alkali metal or alkaline earth metal oxides, carbonates, hydroxides or alkoxides, or amines in substance or dissolved in the esterification alcohol. However, it is also possible to neutralize with basic ion exchangers.

When a column is used in stage 3, the feed to the column is preferably between the top stream and the bottom stream. The excess esterification alcohol ROH, water and corresponding esters of formic acid, acetic acid and propionic acid are drawn off via the top at pressures of from 1 to 1500 hPa, preferably from 20 to 1000 hPa, more preferably from 40 to 800 hPa, and temperatures between 0 and 150° C., preferably 15 and 90° C. and especially 25 and 75° C. This stream can either be incinerated or preferably worked up further in stage 11.

The bottoms obtained are an ester mixture which consists predominantly of the esters of the alcohol ROH used with dicarboxylic acids such as adipic acid and glutaric acid, hydroxycarboxylic acids such as 6-hydroxycaproic acid and 5-hydroxyvaleric acid, and oligomers and free and esterified 1,4-cyclohexanediols. It may be advisable to permit a residual content of water and/or alcohol ROH up to 4% by weight in each case in the ester mixture. The bottom temperatures are preferably from 70 to 250° C., preferably from 80 to 220° C., more preferably from 100 to 190° C.

The stream from stage 3 which has been substantially freed of water and esterification alcohol ROH is fed into stage 4. This is a distillation column in which the feed is between the low-boiling components and the high-boiling components. The column is operated at temperatures of from 10 to 300° C., preferably from 20 to 270° C., more preferably from 30 to 250° C., and pressures of from 1 to 1000 hPa abs., preferably from 5 to 500 hPa, more preferably from 10 to 200 hPa.

The top fraction consists predominantly of residual water and residual alcohol ROH, esters of the alcohol ROH with monocarboxylic acids, predominantly $C_3$- to $C_6$-mono-carboxylic esters with hydroxycarboxylic acids such as 6-hydroxycaproic acid, 5-hydroxyvaleric acid and in particular the diesters with dicarboxylic acids such as adipic acid, glutaric acid and succinic acid, cyclohexanediols, $\epsilon$-caprolactone and valerolactone.

The components mentioned may be removed together via the top or, in a further preferred embodiment, in the column of stage 4 in a top stream which comprises predominantly residual water and residual alcohol and the above-mentioned constituents having from 3 to 5 carbon atoms, and a side stream which comprises predominantly the abovementioned constituents of the $C_6$ esters. The stream comprising the esters of $C_6$ acids, either as an overall top stream or as a side stream, can then, according to how much $\epsilon$-caprolactone is to be prepared, be fed only partly or as the entire stream into stage 12 in the process preferred according to WO 97/31 883.

The high-boiling components of the stream from stage 4, predominantly consisting of dimeric or oligomeric esters, cyclohexanediols and undefined constituents of the DCS, some of which are polymeric, are removed via the stripping section of the column of stage 4, and may either be incinerated or, in a preferred embodiment for so-called transesterification, pass into the stage 8 described in WO 97/31 883.

Stages 3 and 4 may be combined, especially when only relatively small amounts are processed. To this end, for example, the $C_6$ ester stream can be obtained in a fractional distillation performed batchwise.

For the $\epsilon$-caprolactone preparation, the stream from stage 4 comprising predominantly esters of the $C_6$ acids is used. To this end, this stream is separated in stage 12, a distillation column, into a stream comprising predominantly adipic diester via the top and a stream comprising predominantly 6-hydroxycaproic ester via the bottom. The column is operated at pressures of from 1 to 500 hPa abs., preferably from 5 to 350 hPa, more preferably from 10 to 200 hPa, and bottom temperatures of from 80 to 250° C., preferably from 100 to 200° C., more preferably from 110 to 180° C. The top temperatures are established correspondingly.

What is important for a high purity and high yield of $\epsilon$-caprolactone is the removal of the 1,2-cyclohexanediols from the hydroxycaproic ester, since these components form azetropes with one another. It was not foreseeable in this stage 12 that the separation of the 1,2-cyclohexanediols and of the hydroxycaproic ester succeeds completely, in particular when the ester used is the preferred methyl ester.

It may be advantageous also to remove some hydroxycaproic ester in stage 12 together with the adipic diester. The contents in the adipic ester of hydroxycaproic ester are, when the adipic diester is to be hydrogenated to 1,6-hexanediol, advantageously between 0.2 and 7% by weight. According to the alcohol component of the esters, this proportion of hydroxycaproic ester is removed together with the adipic diester via the top (e.g. methyl ester) or via the bottom (e.g. butyl ester).

The stream comprising 6-hydroxycaproic ester is converted in the liquid phase to alcohol and $\epsilon$-caprolactone. It may also comprise further components which may make up a proportion by weight of up to 20%, but preferably a proportion below 10%, more preferably below 5%. These components consist, for example, of 1,5-pentanediol, cyclohexanediols, unsaturated adipic diesters, pimelic diesters, $\epsilon$-caprolactone, 5-hydroxycaproic ester and diesters based, inter alia, on 6-hydroxycaproic esters.

The reaction is performed without catalyst or preferably in the presence of a catalyst. Suitable catalysts are acidic or basic catalysts which may be present in homogeneously dissolved or heterogeneous form. Examples are alkali metal and alkaline earth metal hydroxides, oxides, carbonates, alkoxides or carboxylates, acids such as sulfuric acid or phosphoric acid, organic acids such as sulfonic acids or mono- or dicarboxylic acids, or salts of the aforementioned acids, Lewis acids or Lewis bases, preferably from main group III. and IV. or transition group I. to VIII. of the Periodic Table of the Elements.

Preference is given to using the same catalysts which are also used in stage 8, since the high-boiling discharge stream of stage 13 comprises oligomeric hydroxycaproic acid units which can advantageously be utilized again by means of stage 8. When a heterogeneous catalyst is used, the catalyst hourly space velocity is typically from 0.05 to 5 kg of reactant/l of catalyst and hour. In the case of homogeneous catalysts, the catalyst is preferably added to the reactant stream. The concentration is typically from 10 to 10 000 ppm, preferably from 50 to 5000 ppm, more preferably from 100 to 1000 ppm. The reaction is performed typically at from 150 to 400° C., preferably from 180 to 350° C., more preferably from 190 to 330° C., and pressures of from 1 to 1020 hPa, preferably from 5 to 500 hPa, more preferably from 10 to 200 hPa.

In some cases, it is advantageous to perform the cyclization reaction in the presence of high-boiling mono-, di- or polyols, for example decanol, undecanol, tridecanol, pentadecanol, octadecanol, 1,4-butanediol, 1,5-pentanediol, 1,6-hexanediol, 1,4-cyclohexanediols, butylethylpropanediol, neopentyl glycol, triethylene glycol, tetraethylene glycol, trimethylolpropane or glycerol.

These high-boiling alcohols or polyols are initially charged and/or added or metered separately to the reaction mixture, for example in each case in concentrations of from 0.1 to 90% by weight, preferably from 1 to 60% by weight, more preferably from 5 to 30% by weight.

The reaction products, predominantly esterification alcohol ROH and $\epsilon$-caprolactone, are predominantly removed from the reaction mixture in gaseous form. An advantageous feature is a column attached to the reaction vessel, in which as yet unconverted reactant can be retained in the reaction system, and the alcohol and $\epsilon$-caprolactone can be drawn off via the top. In this case, the product stream can be condensed by fractional condensation, i.e. first predominantly $\epsilon$-caprolactone, then the esterification alcohol. Of course, it is then also possible to obtain only the alcohol via the top, but ε-caprolactone in a side stream. The alcohol stream may advantageously be recycled into stage 2, 8 or 11. The bottom product of the cyclization consists of a complex mixture of oligomers and polymers.

The feed to the reaction vessel can be effected without preheating. When homogeneous catalysts are used, it is advantageous to introduce the reactant stream directly into the cyclization bottoms. In this case, the catalyst can either be added to the feed actually before the reaction or be added directly to the reaction vessel.

However, it is more advantageous to preheat the feed, in particular when the catalyst is already dissolved and a hydroxycaproic ester with a $C_1$-$C_5$-alkohol component is used. The preheating temperature is between 100 and 300° C., preferably from 130 to 270° C., more preferably from 150 to 250° C. At these temperatures, the hydroxycaproic ester already reacts partly to give alcohol, ε-caprolactone and dimeric or oligomeric hydroxycaproic esters. This has the effect that only a small amount of hydroxycaproic ester, when it gets into the hot reaction vessel, can distill immediately out of the reaction bottom. In this way, column trays are dispensed with.

A further advantageous possibility consists in obtaining the predominant portion of the esterification alcohol before the workup of the ε-caprolactone, in particular when this alcohol, such as methanol, has a low boiling point and would consequently be condensable only in a complicated manner. To this end, the methyl hydroxycaproate is preheated as described above in the presence of a catalyst, in which case the alcohol released is already distilled off. This is done advantageously at from 100 to 1100 hPa abs., a pressure range in which the ester alcohol is readily condensable. This method is possible preferably in the presence of the above-described high-boiling alcohols.

According to the invention, the nonvolatile bottom product of the 6-hydroxycaproic ester cyclization is subjected to a thermal treatment batchwise or continuously in a reaction vessel under reduced pressure.

The top stream of the cyclization (FIG. 1, stage 13) is worked up further after condensation in stage 14. This may comprise one or more columns. When one column is used, any esterification alcohol still present and other $C_1$- to $C_6$ low boilers are removed via the top, pure ε-caprolactone is removed via the side stream, and any as yet unconverted hydroxycaproic ester is removed via the bottom and is recycled.

Highly pure ε-caprolactone is obtained when, in stage 14, the low boilers mentioned in a first column via the top, ε-caprolactone and other high boilers are fed via the bottom into a second column, where ε-caprolactone is drawn off via the top. When the ε-caprolactone stream to be obtained comprises only relatively small amounts, ε-caprolactone can be obtained with a column by batchwise fractional distillation.

The condensed top products of the thermal treatment, which, under conditions of thermal treatment, comprise volatile compounds, principally ε-caprolactone, can be worked up by distillation in the same way as the condensed top products of the cyclization, the compounds which are volatile under conditions of cyclization, to give highly pure ε-caprolactone.

In this case, it may be advisable to combine the two top products and to work them up by distillation together as described.

However, it may also be advantageous to work up the two top products separately to give highly pure ε-caprolactone.

The single-stage or multistage distillations to purify the caprolactone are performed at bottom temperatures of from 70 to 250° C., preferably from 90 to 230° C., more preferably from 100 to 210° C., and pressures of from 1 to 500 hPa abs., preferably from 5 to 200 hPa, more preferably from 10 to 150 hPa.

The process is illustrated in detail with reference to the examples which follow, but is in no way restricted by them.
CL EXAMPLES Example 1

Cyclization 1000 g/h of a mixture of approx. 93% methyl 6-hydroxycaproate, 1.0% dimethyl adipate, 1.6% 1,4-cyclohexanediols, 1.4% 1,5-pentanediol, 0.3% unsaturated dimethyl adipate, 0.2% dimethyl pimelate, 1.6% dimeric esters and further compounds which were present in amounts each below 0.1%, prepared according to WO 97/31 883, were pumped together with 1000 ppm of titanate (mixture of isopropyl (80%) and n-butyl titanates (20%)) and 50 g/h of 1,6-hexanediol into a 5 liter reactor with attached column for cyclization. The level in the reactor was kept at approx. 40% by means of closed-loop control. Excess reactor contents were discharged. The reactor contents were pumped in circulation, in the course of which a heat exchanger supplied energy to the system in a pumped circulation system. At a reactor temperature of approx. 220° C. and a pressure of 40 hPa absolute, predominantly methanol and ε-caprolactone distilled off at a reflux ratio of 5:1 per hour. The distillate stream was condensed at approx. 10° C. The gas chromatography analysis showed a yield of ε-caprolactone of 65 mol %.

Thermal Treatment

The liquid reaction effluent from the cyclization reactor (the bottom product of the cyclization) was collected and heated batchwise with addition of a further 1000 ppm of titanate in a distillation still of capacity 2 liters and attached column (reflux ratio 1:1) at 250° C. and 10 hPa absolute for 3 hours. The distillation product obtained comprises predominantly ε-caprolactone and 1,6-hexanediol. The molar ε-caprolactone yield in this second reaction stage in the individual reactions was around 25% ε-caprolactone, such that a yield of 90 mol % was achieved over the overall process. The product obtained in the cyclization and the thermal treatment was distilled batchwise at approx. 40 mbar. This afforded caprolactone with a purity of 99.90%.

Example 2

Thermal Treatment

Example 1 was repeated, with the difference that, in the thermal treatment performed batchwise, 0.2 kg of $C_{15}$-alcohol was added per kg of liquid reaction effluent from the cyclization reactor. This allowed the caprolactone yield in the thermal treatment to be increased to approx. 30%.

The purifying distillation analogous to Example 1 gave a caprolactone purity of 99.92%.

Example 3

Cyclization 20 kg of the 6-hydroxycaproic acid-containing reactant according to Example 1 were mixed with 5 kg of 1,5-pentanediol and, after addition of 1000 ppm of titanate (mixture of isopropyl and n-butyl titanates), heated at standard pressure to 180° C. for 5 hours. During this time, predominantly methanol distilled off. The remaining residue was conveyed continuously at 20 mbar absolute and 240° C. into a wiped-blade evaporator (Sambay). The distillate formed comprised predominantly caprolactone and 1,5-pentanediol. The yield of caprolatone was approx. 80 mol %.

Thermal Treatment

The remaining bottom product of the cyclization was thermally treated in a 5 liter reactor with attached column after another 1000 ppm of titanate had been added. The reactor contents were pumped in circulation, in the course of which a heat exchanger supplied energy to the system in a pumped circulation system. At a reactor temperature of approx. 230° C. and a pressure of 10 hPa absolute, predominantly $\epsilon$-caprolactone distilled off at a reflux ratio of 1:1 per hour. In the resulting distillate, a further 12 mol % of caprolactone was still present. The purifying distillation analogous to Example 1 gave a caprolactone purity of 99.89%.

The invention claimed is:

1. A process for preparing $\epsilon$-caprolactone in a purity of more than 99%, the process comprising:
    (c) cyclizing a 6-hydroxycaproic ester in a liquid phase at from 150 to 400° C. and from 1 to 1020 hPa abs.;
    (d) removing and condensing any compounds which are volatile under cyclization conditions, to separately obtain $\epsilon$-caprolactone and a remaining bottom product;
    (e) thermally treating the remaining bottom product from the cyclizing (c) in at least one further reactor in the presence of from 0.1 to 90% by weight of at least one further alcohol comprising a monool, diol, or polyol, to obtain a treated bottom product;
    (f) removing and condensing any volatile compounds from the treated bottom product, to obtain a condensate; and
    (g) distilling the condensate to obtain the $\epsilon$-caprolactone from the condensate,
    wherein the further alcohol has a boiling point above a boiling point of caprolactone under reaction conditions.

2. The process of claim 1, wherein the thermally treating (e) of the remaining bottom product of the cyclizing (c) is performed at a temperature up to 100° C. above the temperature of the cyclizing (c).

3. The process of claim 1, wherein the thermally treating (e) is effected at a pressure below 50 hPa.

4. The process of claim 1, wherein the remaining bottom product of the cyclizing (c) is thermally treated for from 0.1 to 24 h.

5. The process of claim 1, wherein the thermally treating (e) is performed continuously or batchwise.

6. The process of claim 1, further comprising:
    (a) esterifying a carboxylic acid mixture comprising adipic acid, 6-hydroxycaproic acid, and a 1,4-cyclohexanediol, which is a by-product of oxidizing cyclohexane to cyclohexanone/cyclohexanol with oxygen or at least one oxygen-comprising gas, obtained by water extraction of an oxidation reaction mixture, with a low molecular weight alcohol to produce a carboxylic ester in an esterification mixture; and
    (b) separating the esterification mixture thus obtained in at least one distillation stage so as to obtain a stream comprising at least one 6-hydroxycaproic ester.

7. The process of claim 6, wherein methyl 6-hydroxycaproate is prepared by a process comprising:
    (b1) freeing the esterification mixture of excess methanol and low boilers in a first distillation stage;
    (b2) from the remaining bottom product, in a second distillation stage, performing a separation into (b2-i) an ester fraction essentially free of 1,4-cyclohexanediols and (b2-ii) a fraction comprising at least a majority of the 1,4-cyclohexanediols; and
    (b3) removing methyl 6-hydroxycaproate stream from the ester fraction (b2-i) in a third distillation stage.

8. The process of claim 1, wherein the cyclizing (c) is performed in the presence of 1,6-hexanediol.

9. The process of claim 1, wherein the further alcohol is added to the remaining bottom product of the cyclizing (c) before the thermal treatment.

10. The process of claim 1, wherein the further alcohol is added to the remaining bottom product of the cyclizing (c) during the thermal treatment.

11. The process of claim 1, wherein the 6-hydroxycaproic ester in the cyclizing (c) comprises methyl 6-hydroxycaproate.

12. The process of claim 1, wherein the 6-hydroxycaproic ester in the cyclizing (c) consists essentially of methyl 6-hydroxycaproate.

13. The process of claim 1, wherein the thermally treating (e) is carried out in the presence of from 1 to 60% by weight of the further alcohol.

14. The process of claim 1, wherein the thermally treating (e) is carried out in the presence of from 5 to 90% by weight of the further alcohol.

15. The process of claim 1, wherein the thermally treating (e) is carried out in the presence of from 5 to 30% by weight of the further alcohol.

16. The process of claim 1, wherein the thermally treating (e) is carried out at a temperature of from 180 to 350° C.

17. The process of claim 1, wherein the thermally treating (e) is carried out at a temperature of from 190 to 330° C.

18. The process of claim 1, wherein the thermally treating (e) is effected at a pressure of from 1 and 30 hPa.

19. The process of claim 1, wherein the reactor in which the thermally treating (e) is carried out comprises an attached distillation column, a wiped-blade evaporator, or a falling-film evaporator.

20. The process of claim 1, wherein the thermally treating (e) is carried out without driving out gaseous reaction products, but rather the gaseous reaction byproducts are subsequently separated in a separating apparatus having at least one theoretical plate and partial liquid product reflux.

* * * * *